United States Patent
Hale et al.

(10) Patent No.: US 9,952,141 B1
(45) Date of Patent: Apr. 24, 2018

(54) METHOD OF CHARACTERIZING A BEAM OF ELECTROMAGNETIC RADIATION IN ELLIPSOMETER AND THE LIKE SYSTEMS

(71) Applicants: Jeffrey S. Hale, Lincoln, NE (US); Craig M. Herzinger, Lincoln, NE (US); Martin M. Liphardt, Lincoln, NE (US)

(72) Inventors: Jeffrey S. Hale, Lincoln, NE (US); Craig M. Herzinger, Lincoln, NE (US); Martin M. Liphardt, Lincoln, NE (US)

(73) Assignee: J.A. WOOLLAM CO., INC., Lincoln, NE (US)

( * ) Notice: Subject to any disclaimer, the term of this patent is extended or adjusted under 35 U.S.C. 154(b) by 188 days.

(21) Appl. No.: 14/999,748

(22) Filed: Jun. 22, 2016

Related U.S. Application Data

(60) Provisional application No. 62/231,083, filed on Jun. 25, 2015.

(51) Int. Cl.
*G01N 21/21* (2006.01)
*G01J 4/04* (2006.01)

(52) U.S. Cl.
CPC ............ *G01N 21/211* (2013.01); *G01J 4/04* (2013.01); *G01N 2201/127* (2013.01)

(58) Field of Classification Search
CPC ........ G01J 4/00; G01J 4/02; G01J 4/04; G01J 2004/001; G01J 2004/004; G01J 2004/005; G01J 2004/007; G01J 2004/008; G01N 21/211; G01N 2021/212; G01N 2021/213; G01N 2021/214; G01N 2021/215; G01N 2021/216; G01N 2021/217; G01N 2021/218; G01N 2201/127; G01N 2201/12746
USPC .................................................. 356/364–370
See application file for complete search history.

(56) References Cited

U.S. PATENT DOCUMENTS

| | | | | |
|---|---|---|---|---|
| 5,872,630 A | * | 2/1999 | Johs | G01J 3/447 250/225 |
| 6,353,477 B1 | * | 3/2002 | Johs | G01J 3/447 356/369 |
| 6,859,278 B1 | * | 2/2005 | Johs | G01N 21/211 356/369 |
| 7,075,649 B1 | * | 7/2006 | Johs | G01N 21/211 356/369 |
| 7,336,361 B1 | * | 2/2008 | Liphardt | G01J 4/00 356/369 |
| 7,468,794 B1 | * | 12/2008 | Liphardt | G01N 21/211 356/369 |
| 7,671,989 B2 | | 3/2010 | Liphardt et al. | |
| 7,872,751 B2 | * | 1/2011 | Liphardt | G01N 21/01 356/364 |
| 8,289,527 B2 | * | 10/2012 | Li | G01B 11/24 356/364 |
| 8,553,218 B2 | * | 10/2013 | Tinnemans | G01N 21/4785 356/237.5 |
| 8,812,277 B2 | | 8/2014 | Li | |
| 9,354,118 B2 | * | 5/2016 | Johs | G01J 4/02 |

(Continued)

*Primary Examiner* — Gordon J Stock, Jr.
(74) *Attorney, Agent, or Firm* — James D. Welch

(57) ABSTRACT

An approach to characterizing beams of electromagnetic radiation such as are applied in ellipsometer and the like systems, involving considering the beam to be comprised of a number of spatially distributed beam rays, each of which is represented mathematically as an effectively independent source.

13 Claims, 2 Drawing Sheets

(56) References Cited

U.S. PATENT DOCUMENTS

2010/0128268 A1* 5/2010 Dainty ................ G01J 4/04
356/367
2011/0246141 A1 10/2011 Li

* cited by examiner

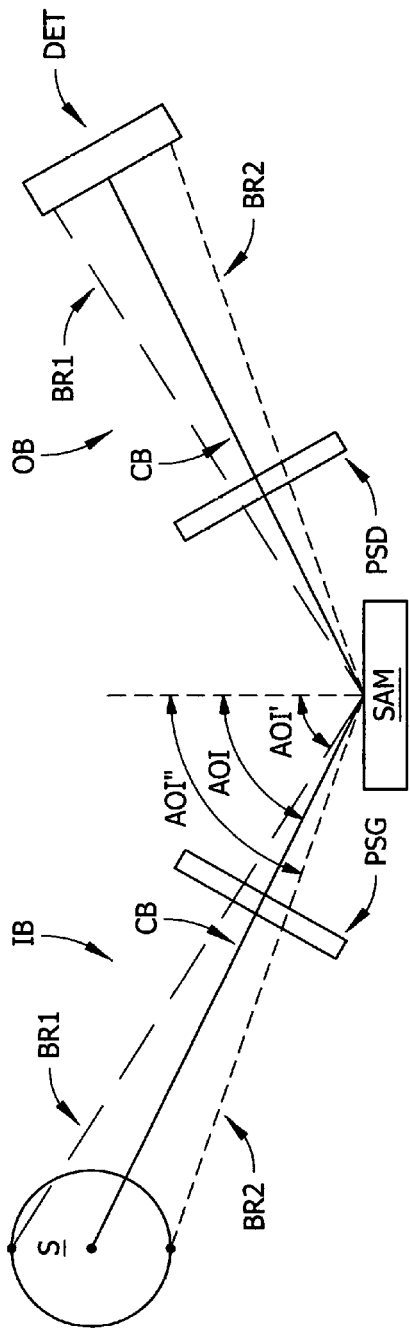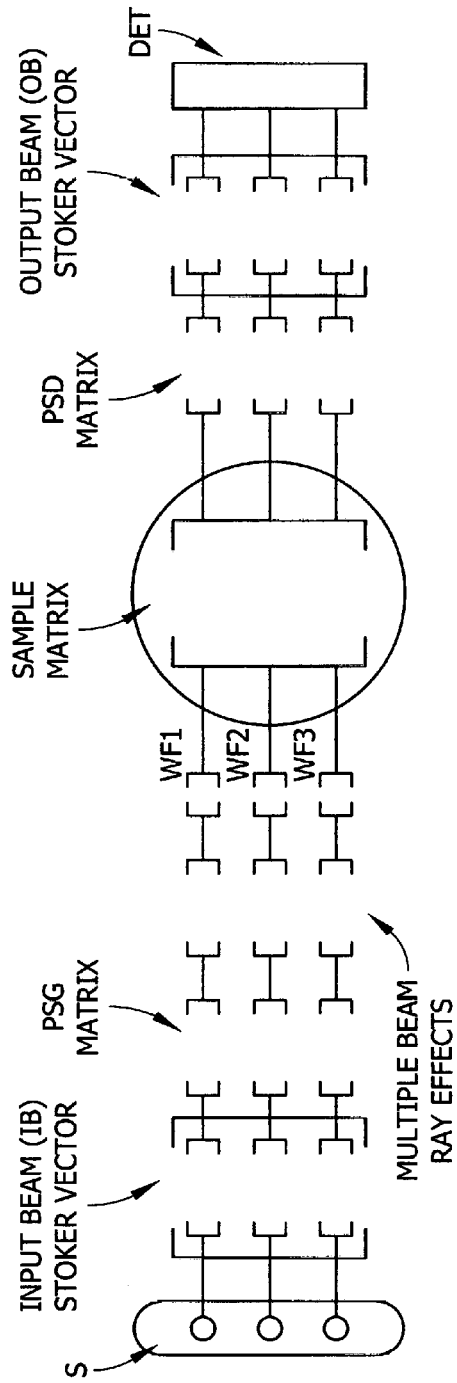

METHOD OF CHARACTERIZING A BEAM OF ELECTROMAGNETIC RADIATION IN ELLIPSOMETER AND THE LIKE SYSTEMS

This Application Claims benefit of Provisional Application 62/231,083, Filed Jun. 25, 2015.

TECHNICAL FIELD

The present invention relates to approaches of directly investigating samples with beams of electromagnetic radiation such as are applied in ellipsometer and the like systems, and more particularly to a method of investigating samples which models a beam as being comprised of a number of spatially separated beam rays, each of which is represented mathematically as an effectively independent source.

BACKGROUND

The use of electromagnetic beams in ellipsometer and the like systems, wherein a single Angle-of-Incidence (AOI) and Plane-of Incidence (POI) of the beam to a sample surface under investigation, (that typically being the (AOI) and (POI) of a Central Beam Ray), is applied in characterizing the sample, is known. This is sufficient in many settings, however, decreasing sample size, increasing demand for measured parameter accuracy and increased information content in beams has led to measurement systems becoming more complex. In newer systems each part of a measurement beam no longer produces equivalent results when compared to other parts. In measurement systems where different parts of a measurement beam produce different sample characterizing data, a single data set representative of the natural addition (or convolution) of these different data sets (from each part of the beam) is produced. And, when this single data set deviates enough from a data set taken with a uniform beam at a single (AOI) and (POI), then a more detailed System calibration and data Analysis procedure is needed that takes into account the different optical paths that each part of the measurement beam experiences. Various parts of a sample investigating beam can produce different results because of different reflection, refraction, coordinate System changes, (AOI), (POI) and general polarization state changes, as well as source beam uniformity, aperture effects and variable attenuation effects. These effects are referred to as Multi beam-ray effects (MBRE) herein. In some cases Multi beam-ray effects are small or trivial such as those that cause simple (AOI) smearing. The Present Invention is concerned with non-trivial Multi beam-ray effects but is also applicable to the trivial cases if desired. The present invention provides particular Utility where some or all of the 16 sample Mueller Matrix elements are used to derive sample Parameters, while in some cases the Mueller Matrix elements themselves are the Parameters of interest.

Results from ellipsometer or the like Systems that experience significant Multi beam-ray effects are improved by application of the present Invention, which seeks to overcome the problems as listed above by subdividing the measurement beam into a certain set of beam-rays. The proposed method includes providing parameterized mathematical models for each beam-ray that takes into account the various multi beam-ray effects, and determining Sample Mathematical model Parameter values in a data Regression calibration step that includes convoluting said parameterized mathematical model. A sample investigation system characterized in a way directed by the present invention is then used to Analyze data from an unknown, (hereafter "sample"), sample to determine Parameter values thereof which are free from considered Multi beam-ray effects and which deviate less from theoretical "true" values than would have been obtained from a "single ray" ellipsometer or the like System.

A known Patent of interest is U.S. Pat. No. 7,671,989 to Liphardt et al. This Patent describes preserving information in a beam of electromagnetic radiation by, when utilized, apertures to, for instance reduce beam size, are applied so as to preserve the angle-of-incidence (AOI) at which the beam is directed toward a sample. That is, equal amounts of beam are interrupted at top, bottom, left and right locations. The beam involved is considered to be a single beam. Another known reference is Published Patent Application No. 2011/0246141 by Li. This reference discloses modeling a beam of electromagnetic radiation as a plurality of rays, and applying said beam to a diffraction grating, (ie. a "structured" sample), which is fabricated in close proximity to a workpiece, such as a wafer, photomask or magnetic medium. For emphasis, Li 141 teaches that the beam of electromagnetic radiation involved is caused to diffract off a periodic structure which is fabricated near a simultaneously fabricated workpiece, and the diffracted electromagnetic radiation is analyzed. Insight to whether or not the workpiece was fabricated correctly is obtained from analysis of the diffracted beam, (ie. a structured sample) as opposed to investigating the workpiece directly. For insight at this point, it is noted that the present invention does not require use of a structured diffraction producing system to determine characteristics of a sample under investigation, but rather applies electromagnetic radiation to directly investigate samples.

DISCLOSURE OF THE INVENTION

The present invention is a method of directly characterizing samples with a beam of electromagnetic radiation, which does not require use of a separately investigated structured system, (eg. a diffraction grating as in Published Patent Application No. 2011/0246141 by Li), comprising the steps of:

a) providing a source of a beam of electromagnetic radiation and considering a beam produced thereby as a composite of a plurality of spatially distributed beam rays;

b) causing said produced beam of electromagnetic radiation to pass through a polarization state generator and become a polarized beam of electromagnetic radiation;

c) causing the resulting polarized electromagnetic beam to interact with a calibration sample at an effective set central ray angle of incidence, and an effective set central ray plane of incidence, and then enter a polarization state detector prior to a data detector, in which data detector data is produced;

d) for each of the plurality of spatially distributed beam rays performing a calibration procedure that effectively treats each beam ray as a separate source of electromagnetic radiation, said calibration procedure involving a simultaneous regression of said data produced in step c) onto a mathematical model of said non-structured calibration sample and of mathematical matrix representations that account for all other beam affecting elements with which said beam interacts, for each beam ray, such that said values for parameters in mathematical matrix representations that account for all other beam affecting elements for each beam ray with which said beam interacts, are established and fixed.

The method continues with:

e) replacing said non-structured calibration sample with a sample and causing a polarized electromagnetic beam produced as in step b) to interact with said sample at an effective set central ray angle of incidence, and an effective set central ray plane of incidence, and then enter a polarization state detector prior to a data detector, in which data detector data is produced;

f) performing a simultaneous regression of said data acquired in step e) onto a mathematical model for said sample and said calibrated mathematical matrix representations that account for all other beam affecting elements with which said beam interacts, for each of said plurality of beam rays, to arrive at values for parameters in said sample characterizing mathematical model.

Said method can involve at least one weighting factor being applied to at least one of said calibrated and fixed mathematical matrix representations that account for said all other beam affecting elements, in addition to said sample, with which said beam interacts.

Said at least one weighting factor can be applied to account for the effects of the shape of an aperture placed into the path of said plurality of beam rays.

Said at least one weighting factor can also account for the effects of different attenuations encountered by different beam rays in said beam of electromagnetic radiation that is considered as a composite of a plurality of spatially distributed beam rays.

The beam of electromagnetic radiation is typically comprised of a plurality of wavelengths and in step e) data is produced in said data detector for at least some of said plurality of wavelengths, and wherein said step f) simultaneous regression of said data acquired in step e) onto a mathematical model for said sample and said calibrated mathematical matrix representations that account for all other beam affecting elements with which said beam interacts, for each of said plurality of beam rays and wavelengths, provides at values for parameters in said sample characterizing mathematical model for said at least some of said plurality of wavelengths.

Said—all other beam affecting elements—for each beam ray with which said beam interacts, can be present between at least one selection from the group consisting of:
said source and said polarization state generator;
said polarization state generator and said polarization state detector;
said polarization state detector and said data detector.

Said calibrated mathematical matrix representations that account for said—all other beam affecting elements—with which said beam interacts account for at least one selection from the group consisting of:
Fresnel refraction;
reflections;
aberrations;
phase changes;
coordinate system rotations;
attenuations;
polarization changes;
angle of incidence changes; and
plane of incidence changes.

It is to be understood that all typical ellipsometer calibration parameters are also to be considered in the terminology "values for parameters in mathematical matrix representations that account for all other beam affecting elements for each beam ray with which said beam interacts, are established and fixed". These include, for instance:
polarizer and analyzer azimuthal angle orientations;
compensator azimuthal angle orientations(s);
detector element image persistence and readout nonlinearities.

Said method can further involve that said calibration sample comprises a selection from the group consisting of:
one non-structured calibration sample, optionally comprising at least one thin layer; and
two non-structured calibration samples, each optionally comprising at least one thin layer;
and wherein data is obtained from said at least one non-structured calibration sample in step c, using at least one selection from the group consisting of:
at least two different central beam angles-of-incidence; and
at least two different central beam planes-of-incidence.

And again, —all other beam affecting elements—as indicated above, accounted for in a simultaneous regression onto all data, whether acquired using one or more non-structured calibration samples. Different non-structured calibration sample mathematical models must be used for different data sets when more than one non-structured calibration sample is involved, however.

U.S. Pat. No. 5,872,630 to Johs et al., and other Patents identify many such parameters that characterize typical ellipsometer or the like systems, and all such parameters are incorporated by reference hereinto.

A preferred number and configuration of spatially distributed beam rays in said composite of a plurality thereof in said electromagnetic beam can be determined by repeating steps a-f, using different selected numbers and/or configurations of spatially distributed beam rays, and determining where convergence occurs and further changes therein do not result in significant changes in values of determined sample values for parameters in said sample characterizing mathematical model.

A preferred number and configuration of spatially distributed beam rays in said composite of a plurality thereof in said electromagnetic beam can alternatively be determined by repeating steps a-f using mathematical simulation to determine a relatively optimum beam of electromagnetic radiation configuration of a plurality of spatially distributed beam rays, comprising the steps of:

a') mathematically simulating a source of a beam of electromagnetic radiation and considering a mathematically simulated beam produced thereby as a composite of a plurality of mathematically simulated spatially distributed beam rays;

b') mathematically simulating passage of said mathematically simulated beam of electromagnetic radiation through a mathematically simulated polarization state generator so that it is becomes a mathematically simulated polarized beam of electromagnetic radiation;

c') mathematically simulating interaction of said resulting mathematically simulated polarized electromagnetic beam with a mathematically simulated calibration sample at an effective set central ray angle of incidence, and an effective set central ray plane of incidence, and then enter a mathematically simulated polarization state detector prior to a mathematically simulated data detector, in which mathematically simulated data detector mathematically simulated data is produced;

d') for each of the plurality of spatially distributed mathematically simulated beam rays performing a calibration procedure that effectively treats each mathematically simulated beam ray as a separate mathematically simulated source of electromagnetic radiation, said calibration procedure involving a simultaneous regression of said mathematically simulated data produced in step c) onto a mathematical model of said mathematically simulated non-structured calibration sample and of mathematical matrix representations that account for all other beam affecting elements with which said mathematically simulated beam interacts, for each mathematically simulated beam ray, such that said values for parameters in mathematical matrix representations that account for all other beam affecting elements for each beam ray with which said beam interacts, are established and fixed;

e') mathematically simulating replacement of said mathematically simulated non-structured calibration sample with a mathematically simulated sample and causing said mathematically simulated polarized beam of electromagnetic radiation interaction with a mathematically simulated sample at an effective set central ray angle of incidence, and an effective set central ray plane of incidence, and then entry into a mathematically simulated polarization state detector prior to entering a mathematically simulated data detector wherein mathematically simulated data is produced;

f') performing a simultaneous regression of said mathematically simulated data acquired in step e) onto a mathematical model for said sample and said calibrated mathematical matrix representations that account for all other beam affecting elements with which said mathematically simulated beam interacts, for each of said plurality of mathematically simulated beam rays, to arrive at values for parameters in said sample characterizing mathematical model;

g') repeating steps a'-f' using different selected numbers and/or configurations of mathematically simulated spatially distributed beam rays, and determining where a convergence in values of determined mathematically simulated sample values for parameters therein occurs;

h') selecting a convergence indicated number and/or configuration of mathematically simulated spatially distributed beam rays, and applying an actual beam of electromagnetic radiation that comprises a plurality of spatially distributed beam rays comprising said number and/or configuration, in an investigation of an actual sample in steps a)-f).

Stated with a broader brush, said mathematical simulation that is first applied to determine a relatively optimum beam of electromagnetic radiation configuration of a plurality of spatially distributed beam rays, includes the steps of:

a) assuming a number and/or configuration of mathematically simulated spatially distributed beam rays and determining values for parameters that characterize a simulated sample;

b) assuming a number and/or configuration of mathematically simulated spatially distributed beam rays which is different than that assumed in step a), and again determining values for parameters that characterize said simulated sample;

c) selecting a criteria for an acceptable convergence of resulting values for parameters that characterize said simulated sample produced in steps a) and b), and repeating steps a) and b) until the results therefrom meet said convergence criteria.

Typically the convergence criteria will be simply that adding more beam rays does not result in results that differ significantly from prior results obtained when fewer beam rays were considered present.

It is also noted that in the above, the terminology "non-structured calibration sample" is to be interpreted to include "at least one non-structured calibration sample, optionally comprising at least one thin layer". Further, the terminology "non-structured", as used herein, is used to avoid reading on a sample that is used to intentionally cause diffraction effects such as the sample disclosed Published Patent Application No. 2011/0246141 by Li.

Finally in this Section, as a general comment to aid with understanding, it is noted that the Matrix calculations in steps d) and d') above are done on a per beam ray basis, but the regression is done on the combination of those calculations. The incoherent Addition of the Matrix calculation produces a single parameterized model based on a data set, (ie. not a data set per beam-ray), obtained from the at least one non-structured calibration sample. This is a simultaneous Regression that simultaneously determines all System Parameters for all the beam-rays. For the purposes of Claim construction, it is to be understood that for each wavelength in a beam of electromagnetic radiation an ellipsometer detector produces a time varying Signal and a plurality of Fourier coefficients are determined therefrom through Fourier transform. A calibration procedure relates these coefficients, (at various frequencies), to Psi and Delta or alternatively Mueller Matrix elements of the sample. That is, for each wavelength one set of PSI and Delta values, or values for Mueller Matrix elements are determined. Extra factors are also usually determined to account for polarization changes from additional elements in the beam path, such as windows or lenses. All of this is done within the Framework of plane electromagnetic waves. Often what has been a standard practice of considering a beam as a single-whole, provides a good approximation. However, when a beam of electromagnetic radiation is—focused—onto a sample said results can be improved by modeling a range of Angles-of-Incidence (AOI's) combined with an averaging calculation. This is termed some AOI smearing. Plane-of-Incidence (POI) smearing is generally ignored because of symmetry, but could be included. The important focus in the present invention is the calibration procedure. Data are collected from at least one non-structured calibration sample, (ie. the sample is not designed to intentionally enter diffraction effects), and a Matrix calculation is performed to generate a parameterized set of data based on optical models of everything the beam encounters, and then Regression Analysis is performed to determine values for the Parameters of everything the beam encounters. Note, importantly, that regarding the present invention, for one non-structured calibration sample one set of Fourier coefficients is generated.

As mentioned in the Background Section, Spectroscopic Ellipsometers (SE's) are progressively becoming more and more complex. Potentially, this means that different parts of a beam yield different results. That fact is hidden from the user who gets only one set of Fourier coefficients per calibration sample, but the results obtained are different for a System where Multi-beam-ray effects are important. The results determined by pre-present invention techniques are often deficient in such a setting and a better procedure is needed to correctly calibrate the ellipsometer or the like system involved. The present Invention recognizes the deficiency and to provide better results breaks up a beam into several beam-rays. That step is done cleverly so that the smallest set of beam-rays that still gives good results is selected for use, (ie. good convergence is achieved). It is important to understand that the present invention does not produce data from a non-structured calibration sample which is fundamentally different from what has been collected in earlier procedures. That is, only one set of Fourier coefficients are determined for a beam of electromagetic radiation, even though said beam is considered to be a combination of many beam-rays. In particular, it is very important to understand that the present invention does not determine different Fourier coefficients for each beam-ray. It would be beneficial if it were possible to determine per beam-ray information, but at present the information achievable is combined together by a "natural averaging" which occurs automatically in the ellipsometer hardware, rather than imposed by software calculations. The present invention parameterizes the problem in a Matrix calculation and a Regression onto the calibration data determines calibration Parameters that are applied when a sample is investigated.

In view of the foregoing, the language in steps d) and d' above and in claim 1, which states "for each beam ray" is not to be interpreted to mean that regression is separately conducted for each beam ray, but rather that regression is simultaneously performed on the calibration data set using mathematical models that take into account each beam-ray separately. Again, as in conventional approaches, only one set of Fourier coefficients for a beam, not multiple sets of Fourier coefficients, on for each modeled beam-ray.

The invention will be better understood by reference to the Detailed Description Section of this Specification, in conjunction with the Drawings.

BRIEF DESCRIPTION OF THE DRAWINGS

FIG. 1 shows a representative Source (S) of a Beam (IB) of electromagnetic radiation comprising Beam Rays (BRI), (CB) and (BR2).

FIG. 2 shows that different regions of a beam of electromagnetic radiation are considered to be from independent sources.

DETAILED DESCRIPTION

Turning now to the Drawings, FIG. 1 shows a representative Source (S) of a Beam (IB) of electromagnetic radiation comprising Beam Rays (BRI), (CB) and (BR2). Note that the Beam (IS) has a finite Diameter and that the Beam rays (BR1) and (BR2) are offset from one another. This example is demonstrative only, and not limiting. In that light, it is to be understood that any number of Beam Rays can be considered as present, and typically a procedure will be performed to determine some optimum configuration prior to practicing the present invention to characterize a sample. Continuing, note that each Beam Ray (BRI),(CB) and (BR2) has its own Angle-of-Incidence (AOI") (AOI) and (AOI') to the Sample Surface, respectively. The important thing as regards the present invention is that each Beam Ray and the components it encounters are mathematically modeled independently, as exemplified in FIG. 2. What the method of the present invention then accomplishes, as presented in the Disclosure Section herein, should be evident from what is shown in said FIGS. 1 and 2. Each Beam Ray is effectively considered as an independent Beam Source, but a simultaneous Regression on all present Beam Rays is applied to arrive at values for the parameters that are found in the various shown Stokes Vector and Matrix Representations. Once the various Stokes Vector and Matrix Representations are calibrated, using a known calibration sample, the values of parameters therein are fixed, and a sample replaces the calibration sample. Importantly, note that "Weighting Factors" (W1), (W2) and (W3) are also indicated. These factors are applied to account for various other elements placed in the path of the Beam (IB) or (OB), such as the shape of apertures(s) or perhaps various Attenuation effecting elements present in the path of the Beam (IS) or (OB). Further, it is to be understood that the Matrix labeled "Multiple Beam Ray Effects" accounts for at least one selection from the group consisting of: Fresnel refraction; reflections; aberrations; phase changes; attenuations; and polarization changes.

Figure 3B:
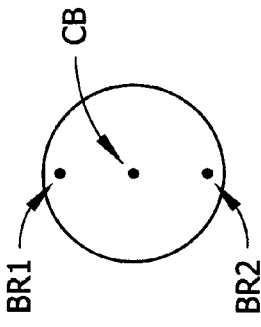
FIGS. 3a-3d demonstrate different models for an electromagnetic beam, looking in cross-section.
Figure 3D:
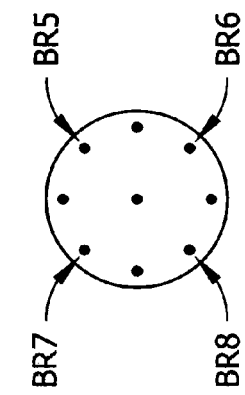
Figure 3A:
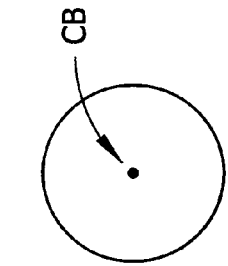
Figure 3C:
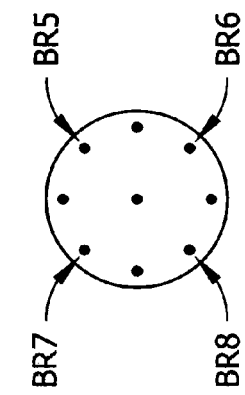

FIGS. 3a-3d are included to demonstrate different models for an electromagnetic beam, looking at it in cross-section. FIG. 3a shows what is common practice, that being to model a beam using only its central ray (CB). FIG. 3b shows a beam model that involves three rays (CB), (BR1) and (BR2), each of which would approach a sample at a different angle of incidence. FIG. 3c shows the addition of two more beam rays (BR3) and (BR4), each of which would approach a sample at a different plane of incidence. FIG. 3d shows addition of rays (BR5), (BR6), (BR7) and (BR8) which would add additional angles and planes of incidence to a sample. FIGS. 3a-3d are exemplary and not limiting. However, it should be appreciated that at some point adding complexity to the beam modeling does not provide much difference in results, compared to a less complex model. An "optimum" level of complexity can be determined by running experiments, or by simulation.

For emphasis, prior to the present invention, electromagnetic beams in ellipsometer and the like systems that investigate samples directly with electromagnetic radiation were modeled with a single Angle-of-Incidence (AOI), that typically being the Central Beam (AOI) in FIG. 1. This is sufficient in many setting, however, where aperture effects, or where different attenuation is applied to different parts of a beam, thereby necessitating different weighting factors (W1), (W2) and (W3) to be applied to various parts of a beam, the method of the present invention is of great utility, particularly in system calibration.

Having hereby disclosed the subject matter of the present invention, it should be obvious that many modifications, substitutions and variations of the present invention are possible in view of the teachings. It is therefore to be understood that the invention may be practiced other than as specifically described and should be limited in breadth and scope only by the Claims.

We claim:

1. A method of directly characterizing samples with a beam of electromagnetic radiation, which does not require use of a separately investigated diffraction producing structured sample, comprising the steps of:
   a) providing a source of a beam of electromagnetic radiation and considering a beam produced thereby as a composite of a plurality of spatially distributed beam rays;
   b) causing said produced beam of electromagnetic radiation to pass through a polarization state generator and become a polarized beam of electromagnetic radiation;
   c) causing the resulting polarized electromagnetic beam to interact with a non-structured calibration sample at an effective set central ray angle of incidence, and an effective set central ray plane of incidence, and then enter a polarization state detector prior to a data detector, in which data detector data is produced;
   d) for each of the plurality of spatially distributed beam rays performing a calibration procedure that effectively treats each beam ray as a separate source of electromagnetic radiation, said calibration procedure involving a simultaneous regression of said data produced in step c) onto a mathematical model of said calibration sample and of mathematical matrix representations that account for all other beam affecting elements with which said beam interacts for each beam ray, such that said values for parameters in mathematical matrix representations that account for all other beam affecting elements for each beam ray with which said beam interacts, are established and fixed;

e) replacing said calibration sample with a sample and causing a polarized electromagnetic beam produced as in step b) to interact with said sample at an effective set central ray angle of incidence, and an effective set central ray plane of incidence, and then enter a polarization state detector prior to a data detector, in which data detector data is produced;

f) performing a simultaneous regression of said data acquired in step e) onto a mathematical model for said sample and said calibrated mathematical matrix representations that account for all other beam affecting elements with which said beam interacts, for each of said plurality of beam rays, to arrive at values for parameters in said sample characterizing mathematical model.

2. A method as in claim 1, wherein at least one weighting factor is applied to at least one of said calibrated and fixed mathematical matrix representations that account for said all other beam affecting elements, in addition to said sample, with which said beam interacts.

3. A method as in claim 2, in which said at least one weighting factor accounts for the effects of the shape of an aperture placed into the path of said plurality of beam rays.

4. A method as in claim 2, in which said at least one weighting factor accounts for the effects of different attenuations encountered by different beam rays in said beam of electromagnetic radiation that is considered as a composite of a plurality of spatially distributed beam rays.

5. A method as in claim 1, wherein the beam of electromagnetic radiation is comprised of a plurality of wavelengths and in step e) data is produced in said data detector for at least some of said plurality of wavelengths, and wherein said step f) simultaneous regression of said data acquired in step e) onto a mathematical model for said sample and said calibrated mathematical matrix representations that account for all other beam affecting elements with which said beam interacts, for each of said plurality of beam rays and wavelengths, provides at values for parameters in said sample characterizing mathematical model for said at least some of said plurality of wavelengths .

6. A method as in claim 1, wherein said all other beam affecting elements for each beam ray with which said beam interacts, are present between at least one selection from the group consisting of:
said source and said polarization state generator;
said polarization state generator and said polarization state detector;
said polarization state detector and said data detector.

7. A method as in claim 1, wherein said calibrated mathematical matrix representations that account for all other beam affecting elements with which said beam interacts account for at least one selection from the group consisting of:
Fresnel refraction;
reflections;
aberrations;
phase changes;
coordinate system rotations;
attenuations;
polarization changes;
angle of incidence changes; and
plane of incidence changes.

8. A method as in claim 1 in which a preferred number and configuration of spatially distributed beam rays in said composite of a plurality thereof in said electromagnetic beam is determined by repeating steps a)-f) using different selected numbers and/or configurations of spatially distributed beam rays, and determining where convergence occurs and further changes therein do not result in significant changes in values of determined sample values for parameters in said sample characterizing mathematical model.

9. A method as in claim 1, in which mathematical simulation is first applied to determine a relatively optimum beam of electromagnetic radiation configuration of a plurality of spatially distributed beam rays, comprising the steps of:

a') mathematically simulating a source of a beam of electromagnetic radiation and considering a mathematically simulated beam produced thereby as a composite of a plurality of mathematically simulated spatially distributed beam rays;

b') mathematically simulating passage of said mathematically simulated beam of electromagnetic radiation through a mathematically simulated polarization state generator so that it is becomes a mathematically simulated polarized beam of electromagnetic radiation;

c') mathematically simulating interaction of said resulting mathematically simulated polarized electromagnetic beam with a mathematically simulated calibration sample at an effective set central ray angle of incidence, and an effective set central ray plane of incidence, and then enter a mathematically simulated polarization state detector prior to a mathematically simulated data detector, in which mathematically simulated data detector mathematically simulated data is produced;

d') for each of the plurality of spatially distributed mathematically simulated beam rays performing a calibration procedure that effectively treats each mathematically simulated beam ray as a separate mathematically simulated source of electromagnetic radiation, said calibration procedure involving a simultaneous regression of said mathematically simulated data produced in step c) onto a mathematical model of said mathematically simulated calibration sample and of mathematical matrix representations that account for all other beam affecting elements with which said mathematically simulated beam interacts, for each mathematically simulated beam ray, such that said values for parameters in mathematical matrix representations that account for all other beam affecting elements for each beam ray with which said beam interacts, are established and fixed;

e') mathematically simulating replacement of said mathematically simulated calibration sample with a mathematically simulated sample and causing said mathematically simulated polarized beam of electromagnetic radiation interaction with a mathematically simulated sample at an effective set central ray angle of incidence, and an effective set central ray plane of incidence, and then entry into a mathematically simulated polarization state detector prior to entering a mathematically simulated data detector wherein mathematically simulated data is produced;

f') performing a simultaneous regression of said mathematically simulated data acquired in step e) onto a mathematical model for said sample and said calibrated mathematical matrix representations that account for all other beam affecting elements with which said mathematically simulated beam interacts, for each of said plurality of mathematically simulated beam rays, to arrive at values for parameters in said sample characterizing mathematical model;

g') repeating steps a'-f' using different selected numbers and/or configurations of mathematically simulated spatially distributed beam rays, and determining where a convergence in values of determined mathematically simulated sample values for parameters therein occurs;

h') selecting a convergence indicated number and/or configuration of mathematically simulated spatially distributed beam rays, and applying an actual beam of electromagnetic radiation that comprises a plurality of spatially distributed beam rays comprising said number and/or configuration, in an investigation of an actual sample in steps a)-f).

10. A method as in claim 1, in which mathematical simulation is first applied to determine a relatively optimum beam of electromagnetic radiation configuration of a plurality of spatially distributed beam rays, including the steps of:

a) assuming a number and/or configuration of mathematically simulated spatially distributed beam rays and determining values for parameters that characterize a simulated sample;

b) assuming a number and/or configuration of mathematically simulated spatially distributed beam rays which is different than that assumed in step a), and again determining values for parameters that characterize said simulated sample;

c) selecting a criteria for an acceptable convergence of resulting values for parameters that characterize said simulated sample produced in steps a) and b), and repeating steps a) and b) until the results therefrom meet said convergence criteria.

11. A method as in claim 1, wherein said calibration sample comprises a selection from the group consisting of:
one non-structured calibration sample, optionally comprising at least one thin layer; and
two non-structured calibration samples, each optionally comprising at least one thin layer.

12. A method as in claim 11, wherein the Matrix calculations in steps d) and d') are done on a per beam Basis, while the regression is done on the combination of those calculations, wherein the incoherent addition of matrix calculation produces a single parameterized model which is regressed onto said single data set as opposed to on a per beam-ray basis, said at least one non-structured calibration sample and said simultaneous regression determines all System Parameters for all the beam-rays, to account for at least one selection from the group consisting of:
Fresnel refraction;
reflections;
aberrations;
phase changes;
coordinate system rotations;
attenuations;
polarization changes;
angle of incidence changes; and
plane of incidence changes.

13. A method as in claim 1, wherein said calibration sample comprises a selection from the group consisting of:
one non-structured calibration sample, optionally comprising at least one thin layer; and
two non-structured calibration samples, each optionally comprising at least one thin layer;
and wherein data is obtained from said at least one non-structured calibration sample in step c, using at least one selection from the group consisting of:
at least two different central beam angles-of-incidence; and
at least two different central beam planes-of-incidence.

* * * * *